(12) United States Patent
Graybill

(10) Patent No.: US 6,409,506 B1
(45) Date of Patent: Jun. 25, 2002

(54) ENDODONTIC INSTRUMENTS AND PROCESS FOR PRODUCING THE SAME

(75) Inventor: Lonnie M. Graybill, York, PA (US)

(73) Assignee: Miltex Dental, Inc., Bethpage, NY (US)

( * ) Notice: Subject to any disclaimer, the term of this patent is extended or adjusted under 35 U.S.C. 154(b) by 0 days.

(21) Appl. No.: 09/563,048

(22) Filed: May 1, 2000

(51) Int. Cl.[7] ................................................. A61C 5/02
(52) U.S. Cl. ....................................................... 433/102
(58) Field of Search ........................ 433/102; 51/94 CS

(56) References Cited

U.S. PATENT DOCUMENTS

| | | | |
|---|---|---|---|
| 4,260,379 A | 4/1981 | Groves et al. | 433/102 |
| 4,611,508 A | 9/1986 | Roane | 76/24 R |
| 4,999,952 A | 3/1991 | Speiser et al. | 51/94 CS |
| 5,065,549 A | 11/1991 | Speiser et al. | 51/288 |
| 5,464,362 A | 11/1995 | Heath et al. | 451/48 |
| 5,527,205 A | 6/1996 | Heath et al. | 451/48 |
| 5,624,259 A | 4/1997 | Heath et al. | 433/72 |
| 5,628,674 A | 5/1997 | Heath et al. | 451/48 |
| 5,653,590 A | 8/1997 | Heath et al. | 433/102 |
| 5,655,950 A | 8/1997 | Heath et al. | 451/48 |
| 5,713,736 A | 2/1998 | Heath et al. | 433/102 |
| 5,807,106 A | 9/1998 | Heath | 433/102 |
| 5,876,202 A | 3/1999 | Berlin | 433/102 |
| 5,882,198 A * | 3/1999 | Taylor et al. | 433/102 |
| 5,921,775 A * | 7/1999 | Buchanan | 433/102 |

* cited by examiner

Primary Examiner—John J. Wilson
(74) Attorney, Agent, or Firm—Pennie & Edmonds LLP

(57) ABSTRACT

Improved endodontic instruments having multiple tapers and instruments which prevent self-feeding or threading into a root canal during root canal therapy on a tooth are provided as well as a process for producing such instruments. The process basically comprises providing a grinding wheel rotated about a first axis having a plurality of flute grinding ribs and an extra flute grinding rib extending from a periphery thereof. A rotating wire stock is fed past the plurality of flute grinding ribs and the extra flute grinding rib at a feed rate and rotation rate such that a separate spiral flute is ground on the wire stock by each of the plurality of flute grinding ribs and the extra grinding rib. The feed rate and rotation rate of the wire stock is changed during the grinding of the instrument whereby the extra grinding rib follows the spiral path of the first flute grinding rib to thereby reduce the number of spiral flutes being ground on the instrument.

23 Claims, 3 Drawing Sheets

ENDODONTIC INSTRUMENTS AND PROCESS FOR PRODUCING THE SAME

BACKGROUND OF THE INVENTION

1. Field of the Invention

The present invention relates to improved endodontic instruments and the manufacture of such instruments by grinding a wire stock.

2. Description of the Prior Art

Endodontic instruments commonly referred to as files are utilized by dentists for cleaning and enlarging the root canals of human teeth. The purpose of the cleaning and enlarging procedure is to remove infected tissue from the root canals and enlarging the root canals so that they can be filled. A commonly used such endodontic instrument is known as a K-type file which has a tapered shaft including three or four spiral flutes along the length thereof. A preferred form of K-file includes three flutes, the cross-sectional shape of the shaft is triangular and the flutes form three spiral cutting edges along the length of the tapered portion of the shaft. Another type of endodontic instrument, known as a reamer, has three or four spiral flutes forming three or four spiral cutting edges thereon. These and other endodontic instruments are manufactured in accordance with standards set up by the American Dental Association and other standardizing bodies.

A problem which is often experienced by dentists in using endodontic instruments like those described above involves the self-feeding or threading of the endodontic instruments into the root canals being enlarged which often causes the instruments to break off in the canals. Another problem associated with the heretofore used endodontic instruments is the requirement that a number of different size instruments having different uniform tapers must be used for each root canal preparation. That is, the dentist must use numerous instruments with different uniform tapers to complete each root canal preparation prior to filling the canal with gutta percha. Thus, there are needs for improved endodontic instruments which do not self-feed into the root canal and which do not require the use of multiple uniform taper instruments.

Various machining processes and apparatus for producing endodontic instruments have been developed and utilized, a particularly suitable process and apparatus are described in U.S. Pat. No. 4,999,952 dated Mar. 19, 1991 and U.S. Pat. No. 5,065,549 dated Nov. 19, 1991, both to Speiser et al., and both of which are incorporated herein and made a part hereof by reference thereto.

While the machining process disclosed in the above mentioned patents to Speiser et al. have been used successfully for the manufacture of endodontic instruments of the types described above, there is a continuing need for improvements to such process whereby improved endodontic instruments can be produced thereby.

SUMMARY OF THE INVENTION

The present invention provides improved endodontic instruments and an improved machining process for manufacturing the instruments which meet the needs described above and overcome the deficiencies of the prior art.

An improved endodontic instrument of this invention adapted for use in performing root canal therapy is basically comprised of an elongate shank having a proximate end, a pilot end and a tapered peripheral surface adjacent the pilot end thereof. A first plurality of continuous helical flutes which form cutting edges on the peripheral surface are formed in and extend along a first portion of the peripheral surface. A second plurality of continuous helical flutes which form cutting edges on the peripheral surface are formed in and extend along a second portion of the peripheral surface adjacent to the first portion thereof. The second plurality of helical flutes contains a number of flutes different from the number of flutes in the first plurality of helical flutes. As a result of the different number of flutes in the pluralities of continuous helical flutes on the peripheral surface of the instrument, the instrument is prevented from self-feeding in a root canal when being used. The endodontic instrument can include additional pluralities of continuous helical flutes which form cutting edges on the peripheral surface formed in and extending along third and additional portions of the peripheral surface, each of the additional pluralities of helical flutes containing a number of flutes different from the number of flutes in adjacent pluralities of helical flutes.

The improved process of this invention for producing the above described endodontic instrument, i.e., an instrument which includes successive pluralities of continuous helical flutes containing different numbers of flutes, which does not self-feed in a root canal basically comprises the following steps. A first grinding wheel rotated about a first axis is provided having a plurality of flute grinding ribs and an extra flute grinding rib extending from a periphery thereof. A rotating wire stock is fed past the plurality of flute grinding ribs and the extra flute grinding rib along a second axis at a first feed rate and rotation rate such that a separate spiral flute is ground on the wire stock by each of the plurality of flute grinding ribs and by the extra grinding rib. The feed rate and rotation rate of the wire stock past the plurality of flute grinding ribs and the extra flute grinding rib are increased so that a separate spiral flute is ground on the wire stock by each of the plurality of flute grinding ribs and the extra flute grinding rib follows the spiral path of the first flute grinding rib to make grinding contact with the wire stock. Optionally, the first feed rate and rotation rate or both the first feed rate and rotation rate and the increased feed rate and rotation rate can be repeated to form one or more additional pluralities of continuous flutes on the instrument. Simultaneously with the grinding of the flutes, the grinding wheel or the wire stock is translated, i.e., moved, such that a distance between the first and second axes increases as the wire stock is fed whereby a single pass of the wire stock past the flute grinding ribs and the rolled deformed metal grinding rib produces a tapered multi-fluted endodontic instrument.

A preferred process of this invention includes the above steps in combination with the following additional steps. First and second tapered grinding surfaces are provided on the grinding wheel for forming a desired form of tip, such as a tapered tip, on the rotating wire stock, and for parting a previously formed multi-fluted tapered endodontic instrument from the rotating wire stock. In addition, a second grinding wheel having a plurality of depth indicating calibration grinding ribs extending from a periphery thereof which is rotated about a third axis is provided. The first grinding wheel is retracted from a flute grinding position with the rotating wire stock to a non-grinding position, and the rotating wire stock is fed forward a predetermined distance. Thereafter, the feed of the rotating wire stock is temporarily terminated while the first and second grinding wheels are advanced into grinding contact with the wire stock whereby a previously formed tapered multi-fluted endodontic instrument is parted from the wire stock, a tip having a desired form is ground on the wire stock and depth indicating calibration grooves are ground on the wire stock. The first and second grinding wheels are retracted whereby the first grinding wheel is returned to the flute grinding position and the second grinding wheel is returned to a position out of contact with the wire stock. The feed of the rotating wire stock is then resumed so that the proper taper and flutes are ground on the wire stock whereupon the above steps are repeated.

Another improved endodontic instrument provided by this invention and produced by the above described process has two or more portions of the fluted tapered peripheral surface thereof of differing taper.

It is, therefore, a general object of the present invention to provide improved endodontic instruments and a process for forming the instruments.

Other and further objects, features and advantages of the present invention will be readily apparent to those skilled in the art upon a reading of the description of preferred embodiments which follows when taken in conjunction with the accompanying drawings.

DESCRIPTION OF PREFERRED EMBODIMENTS

The present invention provides an improved endodontic instrument for use in performing root canal therapy on a tooth. The instrument is basically comprised of an elongated shank having a proximate end, a pilot end and a tapered peripheral surface adjacent to the pilot end. A first plurality of continuous helical flutes which form cutting edges on the peripheral surface is formed in and extends along a first portion of the peripheral surface. A second plurality of continuous helical flutes which form cutting edges on the peripheral surface is formed in and extends along a second portion of the peripheral surface adjacent to the first portion thereof. The second plurality of helical flutes contains a number of flutes different from the number of flutes in the first plurality of helical flutes. For example, the first plurality of continuous helical flutes can contain four flutes and the second plurality of helical flutes can contain three flutes. As a result of the different numbers of flutes formed in the first and second portions of the peripheral surface, the first and second portions have different numbers of spiral cutting edges formed thereon, e.g., four and three, respectively, the spiral cutting edges have different helix angles, e.g., smaller and greater, respectively, and the first and second portions have different cross-sectional shapes, e.g., substantially square and substantially triangular, respectively. Consequently, when the instrument is used for cleaning and enlarging a root canal of a tooth, the presence of the different numbers of cutting edges, the different helix angles and the different cross-sectional shapes along the length of the peripheral surface prevents the instrument from self-threading into the tooth and breaking off. The endodontic instrument can include one or more additional pluralities of continuous helical flutes which extend along a third and additional portions of the peripheral surface of the instrument, each of the additional pluralities of helical flutes containing a number of flutes different from the number of flutes in adjacent pluralities of helical flutes.

Figure 3:
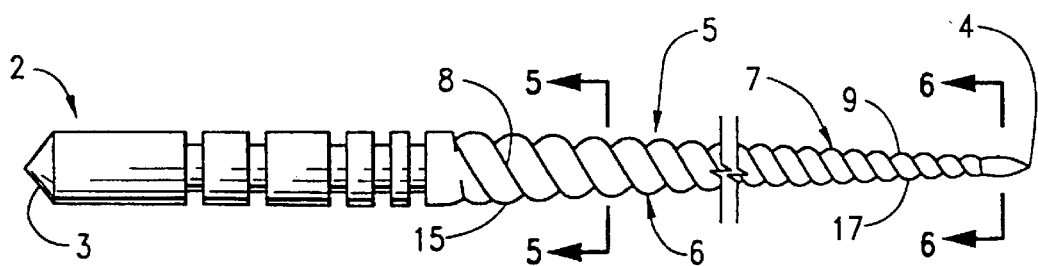
FIG. 3 is an enlarged side view of a tapered endodontic instrument of this invention having successive pluralities of continuous helical flutes containing different numbers of flutes produced by the grinding process of the invention.
Figure 5:
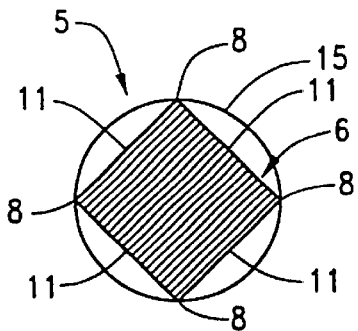
FIG. 5 is an enlarged cross-sectional view taken along line 5—5 of FIG. 3.
Figure 6:
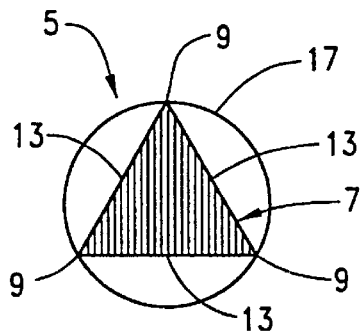
FIG. 6 is an enlarged cross-sectional view taken along line 6—6 of FIG. 3.

Referring now to the drawings and particularly to FIGS. 3, 5 and 6, an endodontic instrument of the present invention having first and second pluralities of continuous helical flutes formed thereon is illustrated and generally designated by the numeral 2. The instrument 2 is comprised of an elongated shank having a proximate end 3 and a pilot end 4. A tapered peripheral surface generally designated by the numeral 5 is formed on the shank adjacent the pilot end 4 thereof. A first plurality of continuous helical flutes 6 which form cutting edges 8 on the peripheral surface 5 is formed in and extends along a first portion 15 of the peripheral surface 5. A second plurality of continuous helical flutes 7 which form cutting edges 9 on the peripheral surface 5 is formed in and extends along a second portion 17 of the peripheral surface 5 adjacent to the first portion thereof. As mentioned, the first and second pluralities of helical flutes 6 and 7 contain different numbers of flutes which makes the numbers of spiral cutting edges 8 and 9, respectively, different, the helix angles of the cutting edges different and the cross-sectional shapes of the first and second portions 15 and 17, respectively, different. These differences prevent the instrument 2 from self-feeding or threading into a root canal being prepared with the instrument.

As shown in FIG. 5, the plurality of flutes 6 includes four flutes 11 and the cross-sectional shape of the peripheral surface 5 containing the flutes 11 is rectangular. As shown in FIG. 6, the plurality of flutes 7 contains three flutes 13 and the cross-sectional shape of the peripheral surface 5 containing the flutes 13 is triangular. Thus, the instrument illustrated in FIG. 3 includes two adjacent pluralities of continuous helical flutes 6 and 7 containing four flutes and three flutes, respectively. As mentioned, more than two pluralities of continuous helical flutes can be formed on the peripheral tapered surface of an endodontic instrument with each of the pluralities of helical flutes on the instrument containing a number of flutes different from the number of flutes in adjacent pluralities of helical flutes.

The improved process of the present invention basically comprises the steps of (a) providing a first grinding wheel rotated about a first axis having a plurality of flute grinding ribs and an extra flute grinding rib extending from a periphery thereof; (b) feeding a rotating wire stock past the plurality of flute grinding ribs and the extra flute grinding rib along a second axis at a feed rate and rotation rate such that a separate spiral flute is ground on the wire stock by each of the plurality of flute grinding ribs and the extra flute grinding rib, (c) feeding the rotating wire stock past the plurality of flute grinding ribs and said extra flute grinding rib at a feed rate and rotation rate such that a separate spiral flute is ground on the wire stock by each of the plurality of flute grinding ribs, but the extra flute grinding rib follows the spiral path of the first flute grinding rib to make grinding contact with the wire stock; and (d) optionally repeating step (b) or both of steps (b) and (c). The first grinding wheel or the wire stock is translated such that a distance between the first and second axes increases as the wire stock is fed whereby a single pass of the wire stock past the flute grinding ribs produces a tapered multi-fluted endodontic instrument.

As will be understood, the extra flute grinding rib is the last rib on the first grinding wheel and contacts the wire stock last. When the extra flute grinding rib follows the path of the first flute grinding rib to make contact with the wire stock, it moves through the first flute formed in the wire stock, and as a result one less flute is formed in step(c) than is formed in step (b).

As will also now be understood, one or more additional pluralities of continuous helical flutes can be formed in the wire stock containing a number of flutes different from the number of flutes in adjacent pluralities of helical flutes.

Other aspects of the process of this invention include simultaneously grinding a tip of desired form on the rotating wire stock, grinding a plurality of depth indicating calibration grooves on the rotating wire stock and parting a previously formed tapered multi-fluted endodontic instrument from the rotating wire stock, all during the single pass of the rotating wire stock mentioned above.

Another aspect of the process involves selectively accelerating the feed rate of the rotating wire stock past the plurality of flute grinding ribs and the extra flute grinding rib whereby the flutes are ground on the small diameter end portions of very small endodontic instruments being produced at a relatively slow rate and at an accelerated feed rate during the grinding of the flutes on the larger diameter portions of the instruments. This reduces the overall instrument producing cycle time for small size endodontic instruments by as much as 40%.

Yet another aspect of the process of this invention involves the use of a coil fed rotating wire stock system. Instead of utilizing bar length wire stock which requires reloading after every bar, a continuous feed reel of coiled wire stock is utilized which reduces reloading time and increases instrument production. The reel of coiled wire stock pays off wire as it is needed and also rotates on the same axis and at the same rate as the endodontic instrument being ground.

Still another aspect of the apparatus of this invention involves the use of an adjustable dressing wheel for dressing the depth indicating calibration forming grinding wheel mentioned above.

Figure 1:
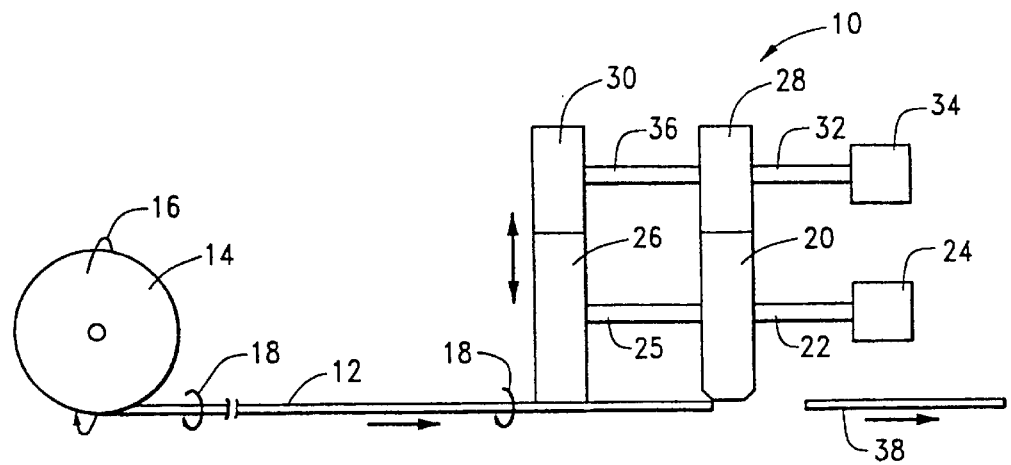
FIG. 1 is a schematic illustration of the improved grinding apparatus of this invention.

Referring again to the drawings, and particularly to FIG. 1, the apparatus of this invention for producing the endodontic instrument 2 described above having a tapered tip and having a predetermined number of depth calibration grooves, all in a single cycle is illustrated. As shown in FIG. 1, a feed wire stock 12 is payed off of a rotatable reel 14 having a continuous coil of wire stock 12 wound thereon. As shown by the arrows 16 and 18, the reel 14 and wire stock 12 are rotated on the same axis and at the same rate as the portion of the wire stock 12 being ground. The rotation of the reel 14 and wire stock 12 is synchronized through a clutch mechanism, and the wire stock is fed using a lead screw mechanism or the like. The rotating feed stock 12 is fed in a direction towards and in contact with a first rotating grinding wheel 20. The grinding wheel 20 is generally disk-shaped and is disposed in a manner whereby its axis of rotation is parallel to the axis of rotation of the feed wire stock 12. A drive shaft 22 connects the first grinding wheel 20 to means for rotating the grinding wheel such as an electric motor 24, and a drive shaft 25 positioned coaxially with the drive shaft 22 connects the first rotating grinding wheel 20 to a second rotating grinding wheel 26. As mentioned above, the first grinding wheel 20 includes a plurality of flute grinding ribs and an extra flute grinding rib for forming flutes on the endodontic instrument being produced. The second grinding wheel 26 includes a plurality of depth indicating calibration groove grinding ribs formed thereon. A dressing wheel 28 is provided for dressing the surface of the first grinding wheel 20 and a second dressing wheel 30 is provided for dressing the surface of the second grinding wheel 26. The first dressing wheel 28 is rotated by a shaft 32 connected to a second rotator, e.g., electric motor 34, and a shaft 36 positioned coaxially with the shaft 32 is connected between the dressing wheels 28 and 30. The axes of the dressing wheel shafts 32 and 36 are positioned parallel to the axes of the grinding wheel shafts 22 and 24. The axis of the rotating wire stock 12 is also positioned parallel to the axes of the shafts 22 and 24. As will be described in detail hereinbelow, after a tapered multi-fluted endodontic instrument 38 is formed on an end portion of the rotating wire stock 12 which has been fed past the first grinding wheel 20. The instrument 38 is simultaneously parted from the rotating wire stock 12 while the tapered tip of the next instrument is ground on the rotating wire stock 12.

Figure 2:
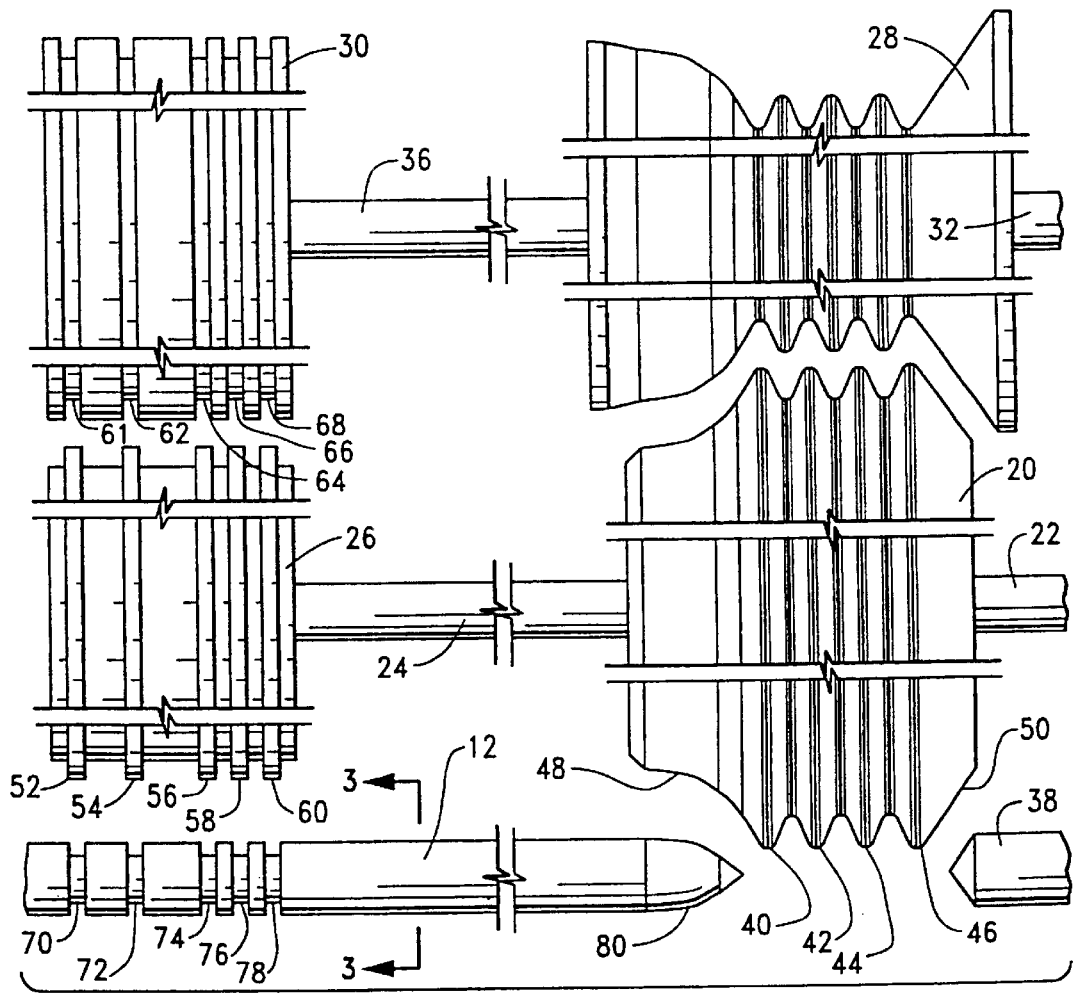
FIG. 2 is a partial enlarged view of the first and second grinding wheels, first and second dressing wheels and the ground wire stock of FIG. 1.

Referring now to FIGS. 2 and 4, the grinding wheel-dressing wheel assembly and the rotating wire stock being ground are illustrated in FIG. 2 and a produced endodontic instrument 38 which is different from the produced instrument 2 described above is illustrated in FIG. 4. That is, the instrument 38 includes two or more tapers which increase from the pilot end toward the opposite end of the tapered peripheral surface containing flutes. The instrument 38 also includes a tapered tip and depth calibration grooves.

As shown in FIG. 2, the first grinding wheel 20 includes on the periphery thereof three flute grinding ribs 40, 42 and 44 and an extra flute grinding rib 46. As is well understood by those skilled in the art, a grinding wheel with three flute grinding ribs is for manufacturing three fluted endodontic instruments. Less or more flute grinding ribs can be included on the grinding wheel for producing endodontic instruments having less or more than three spiraled flutes. As mentioned above and as will be further described below, the extra flute grinding rib 46 of the present invention, i.e., the forth grinding rib on the grinding wheel 20, either forms a forth flute on the instrument produced or follows the spiral path of the first flute grinding rib, i.e., rib 40, whereby three flutes are formed on the instrument produced. In addition, the first grinding wheel 20 includes a tip forming grinding contour 48 and a tapered instrument parting contour 50.

The second grinding wheel 26 includes a plurality of spaced depth calibration groove grinding ribs 52, 54, 56, 58 and 60 formed thereon. The depth calibration grooves on an endodontic instrument serve to provide an indication to the endodontist of the depth to which the tip of the instrument reaches within a root canal being cleaned. Depending on a particular size of the endodontic instruments being produced, more or less depth calibration groove grinding ribs can be included on the second grinding wheel 26, appropriately spaced from each other to provide the required number and spacing of depth calibration grooves on the instrument being manufactured.

The first grinding wheel 20 is rotated by the shaft 22 connected thereto and the shaft 25 connects the first grinding wheel 20 to the second grinding wheel 26 so that the grinding wheels 20 and 26 are rotated at the same rate. In addition, the first and second grinding wheels 20 and 26 are selectively movable towards and away from the rotating wire stock 12 by conventional apparatus (not shown). The dressing wheels 28 and 30 which are rotated simultaneously by means of the shafts 32 and 36 connected thereto are illustrated a distance apart from the first and second grinding wheels 20 and 26 for clarity. However, in operation, the surfaces of the dressing wheels 28 and 30 are periodically or continuously in contact with the peripheries of the grinding wheels 20 and 26, respectively, so as to maintain the shapes of the flute grinding ribs 40, 42 and 44, the extra flute grinding rib 46 and the depth calibration groove grinding ribs described above. As will be understood, if the first grinding wheel 20 includes more or less than four flute grinding ribs, the dressing wheel 28 includes the same number and shape of complimentary grooves therein.

The second dressing wheel 30 includes five complimentary grooves 61, 62, 64, 66 and 68 formed thereon for maintaining the size and shape of the groove grinding ribs 52, 54, 56, 58 and 60 on the second grinding wheel 26. The first and second dressing wheels 28 and 30 are rotated simultaneously by the rotating shafts 32 and 36 connected thereto, and like the grinding wheels 20 and 26, the dressing wheels 28 and 30 are simultaneously movable with the grinding wheels 20 and 26 by conventional apparatus (not shown). Also, the dressing wheels 28 and 30 can be rotated in the same direction as the grinding wheels 20 and 26 but at a selected different rate, or the dressing wheels 28 and 30 can be rotated in the opposite direction from the grinding wheels 20 and 26 at a selected rate. As will be understood, the grinding wheels 20 and 26 are rotated at a rate which is optimum for grinding the metal instrument being formed at the feed rate and rotation rate of the wire stock. In a like manner, the dressing wheels 28 and 30 are rotated at a rate, in a direction and either periodically or continuously in contact with the grinding wheels 28 and 30 which are optimum for dressing the grinding wheels.

As will be described in greater detail hereinbelow and as illustrated in FIG. 2, the wire stock 12 is shown just after depth calibration grooves 70, 72, 74, 76 and 78 have been ground on the wire stock 12 by the depth calibration groove grinding ribs 52, 54, 56, 58 and 60, respectively, of the second grinding wheel 26. Simultaneously with the grinding of the depth calibration grooves 70, 72, 74, 76 and 78, a tapered tip 80 is ground on the leading end of the rotating wire stock 12 by the tapered tip grinding contour 48 of the first grinding wheel 20. Also simultaneously, the previously formed tapered multi-fluted endodontic instrument, i.e., the instrument 38 having a tapered tip and depth calibration grooves thereon is parted off the rotating wire stock 12 by the tapered contour 50 of the first grinding wheel 20. As mentioned above, the first and second grinding wheels 20 and 26 are illustrated in FIG. 2 after the grinding of the depth calibration grooves 70, 72, 74, 76 and 78, after the grinding of the tapered tip 80 and after the parting off of the instrument 38 and the grinding of the spiraled flutes is ready to commence. The ground metal portion of the wire stock 12 between the tapered tip 80 and the parted instrument 38 is discarded.

Figure 4:
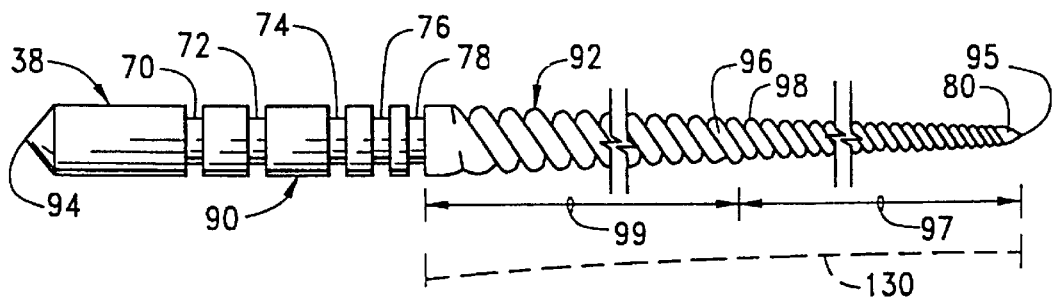
FIG. 4 is an enlarged side view of an endodontic instrument of this invention having fluted portions of differing taper.

Referring now to FIG. 4, the instrument 38 of this invention produced by the apparatus 10 which will be described in detail hereinbelow is shown in its entirety. The instrument 38 includes a shank 90 having a proximate end 94 and a pilot end 95. A handle may be attached to the proximate end portion which includes the depth calibration grooves 70, 72, 74, 76 and 78. The shank 90 includes a tapered peripheral surface 92 which has two portions of different taper and spiraled flutes which extend over the length of the peripheral surface 92 and define a plurality of cutting edges 98 thereon. The peripheral surface 92 of the instrument 38 terminates in the tapered tip 80.

As mentioned above, the wire stock 12 is simultaneously rotated and fed on an axis which is preferably parallel to the axes about which the first grinding wheel 20 and second grinding wheel 26 are rotated. The feed distance in which the wire stock 12 is fed per revolution of the wire stock 12 is referred to herein as the lead distance. The flute grinding ribs 40, 42 and 44 and the extra flute grinding rib 46 of the first grinding wheel 20 are separated from one another by a distance equal to the lead distance of the rotating wire stock 12 during 120° of revolution. The proper tapers are formed on the peripheral surface 92 of the produced instrument 38 by translating either the rotating wire stock 12 or the first grinding wheel 20 by conventional apparatus (not shown) so as to continuously increase the distance therebetween as the wire stock 12 is simultaneously rotated and fed during the grinding of the spiraled flutes 96. The rate at which either the first grinding wheel 20 or the rotating wire stock 12 is translated determines the tapers of the peripheral surface 92.

In the operation of the process of this invention (referring again to FIG. 2), the first and second grinding wheels 20 and 26 are rotated about a first axis (the axes of the shafts 22 and 25), and at the beginning of each endodontic instrument producing cycle, the grinding wheels 20 and 26 are in a retracted position whereby both are out of grinding contact with the rotating wire stock 12. The rotating wire stock 12 is fed forward a predetermined distance, i.e., a distance to move the previously formed depth calibration grooves past the first grinding wheel 20 and to position the tapered grinding contour 50 thereof adjacent the point on the rotating wire stock 12 where the previously formed instrument 38 is to be parted from the rotating wire stock 12. The feed of the rotating wire stock 12 is temporarily terminated while continuing its rotation, and the first and second grinding wheels 20 and 26 are advanced into grinding contact with the rotating wire stock 12 whereby the previously formed endodontic instrument 38 is parted from the rotating wire stock 12, the tapered tip 80 is ground on the wire stock 12 by the tapered tip forming contour 48 of the first grinding wheel 20 and the depth calibration grooves 70, 72, 74, 76 and 78 are ground on the rotating wire stock 12 by the depth calibration groove grinding ribs 52, 54, 56, 58 and 60 of the second grinding wheel 26. After the previously formed instrument 38 has thus been parted from the wire stock 12 and the tapered tip and depth calibration grooves have been formed thereon, the first and second grinding wheels 20 and 26 are retracted whereby the first grinding wheel 20 is in a flute grinding position and the second grinding wheel 26 is in a position out of grinding contact with the wire stock 12 as shown in FIG. 2. Thereafter, the rotating wire stock 12 is fed past the flute grinding ribs 40, 42 and 44 and the extra flute grinding rib 46 on the first grinding wheel 20 so that flutes 96 are ground on the wire stock by the flute grinding ribs 40, 42 and 44, and when desired, by the extra flute grinding rib 46. Simultaneously with the grinding of the flutes 96, the first grinding wheel 20 (and the second grinding wheel 26) or the wire stock 12 are translated such that a distance between the axis of the grinding wheels 20 and 26 and the axis of the rotating wire stock 12 increases as the wire stock 12 is fed so as to cause the peripheral surface 92 of the instrument 38 being produced to include two portions of different taper 97 and 99 which will be described further hereinbelow. After the flutes have been ground, the first and second grinding wheels 20 and 26 are again retracted to a position out of grinding contact with the rotating wire stock 12 and the additional steps in the cycle described above are repeated.

During all or a part of each instrument producing cycle, the first and second dressing wheels 28 and 30 are in contact with the first and second grinding wheels 20 and 26, respectively, so as to maintain the required shapes, heights and distances of the grinding ribs and contours on the grinding wheels.

Figure 8:
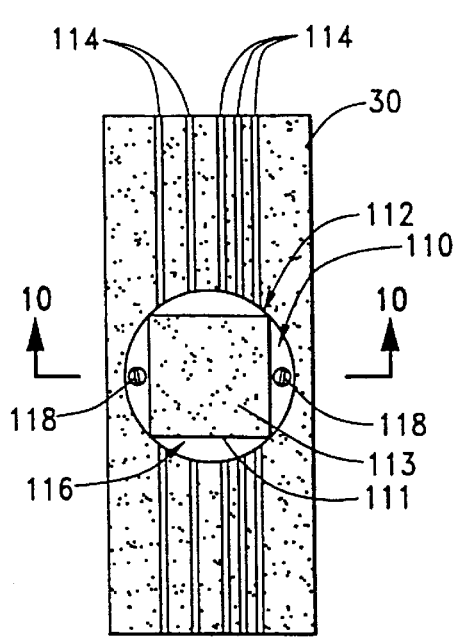
FIG. 8 is a top more detailed view of the second dressing wheel illustrated schematically in FIG. 2.
Figure 9:
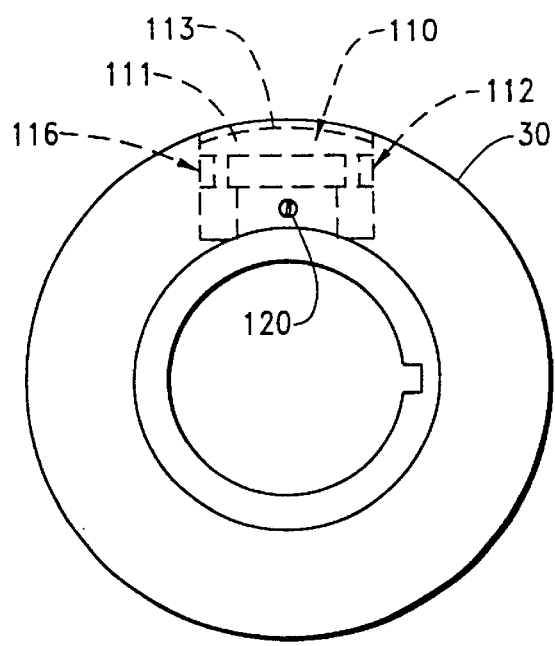
FIG. 9 is a side view of the dressing wheel of FIG. 8.
Figure 10:
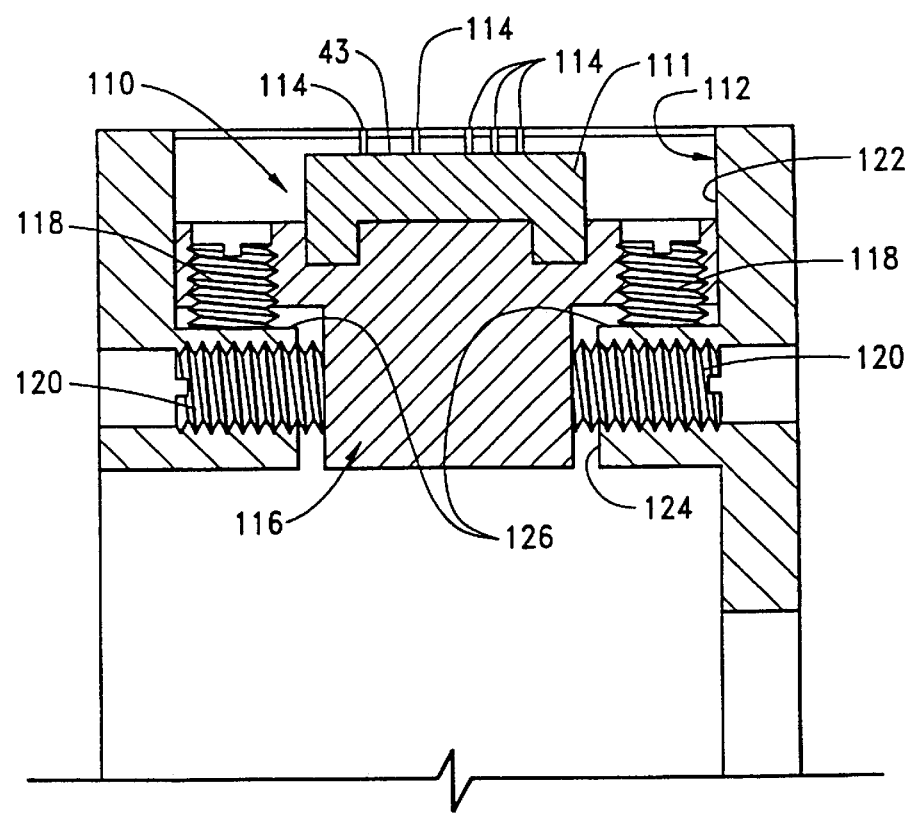
FIG. 10 is a cross-sectional view taken along line 10—10 of FIG. 10.

Referring now to FIGS. 8–10, a preferred form of the second dressing wheel 30 is illustrated which includes a groove depth adjustment assembly 110 for adjusting the heights of the depth calibration groove grinding ribs 52, 54, 56, 58 and 60 on the second grinding wheel 26. The adjustment assembly 110 is cylindrical in overall shape and fits within a cylindrical opening 12 in the dressing wheel 30 as best illustrated in FIGS. 9 and 10. The assembly 110 includes an insert 111 which has an arcuate diamond abrasive coated top surface 113. The insert 111 is positioned whereby it forms the bottom surface of the spaced grooves 114 formed in the diamond abrasive coated periphery of the dressing wheel 30.

The insert 111 is sealingly attached to a pedestal 116 which is adjustable in height by a pair of vertical set screws 118 and is locked in place by a pair of horizontal set screws 120. That is, as best shown in FIG. 11, the opening 112 in the grinding wheel 130 includes an enlarged upper bore 122 which intersects a smaller counterbore 124. The smaller counterbore 124 forms an annular shoulder 126 within the opening 112. The set screws 118 of the assembly 110 are threadedly connected to the pedestal 116 and rest on the annular shoulder 126. As mentioned, the set screws 118 are used to adjust the height of the surface 113 of the insert 111 with respect to the grooves 114. As will now be understood, by adjusting the height of the surface 113, the heights of the depth calibration groove grinding ribs 52, 54, 56, 58 and 60 formed on the second grinding wheel 26 by the second dressing wheel 30 are correspondingly adjusted. In order to lock the assembly 110 in the dressing wheel 30, the set screws 120 are tightened against the pedestal 116.

The dressing wheel 30 can include more than one cylindrical opening 112 and assembly 110 positioned around the periphery thereof. Preferably, two or more of the assemblies 110 are utilized. As will also now be understood, as the dressing wheel 30 is rotated against the peripheral surface of the grinding wheel 26, the arcuate surface 113 of the insert 111 contacts and adjusts the heights of the depth calibration groove grinding ribs on the grinding wheel 26.

The improved process of the present invention for producing endodontic instruments having successive pluralities of continuous helical flutes containing different numbers of flutes basically comprises the following steps. A first grinding wheel is rotated about a first axis having a plurality of flute grinding ribs and an extra flute grinding rib extending from a periphery thereof. A rotating wire stock is fed past the plurality of flute grinding ribs and the extra flute grinding rib along a second axis at a feed rate and a rotation rate such that a separate flute is ground on the wire stock by each of the plurality of flute grinding ribs and by the extra flute grinding rib. After a first plurality of continuous helical flutes which form cutting edges on a first portion of the wire stock have been formed in the wire stock, the feed rate and rotation rate of the wire stock is changed such that a separate spiral flute is ground on the wire stock by each of the plurality of flute grinding ribs, but the extra flute grinding rib follows the spiral path of the first flute grinding rib that made contact with the wire stock after the rates were changed. As a result, a second plurality of continuous helical flutes is formed on a second portion of the wire stock adjacent to the first portion containing the first plurality of flutes which has one less spiral flute than the first plurality of flutes.

While grinding the above mentioned flutes, the first grinding wheel or the wire stock is translated, i.e., moved, such that a distance between the axis of the grinding wheel and the axis of the rotating wire stock increases as the wire stock is fed whereby a single pass of the rotating wire stock past the flute grinding ribs produces a tapered multi-fluted endodontic instrument.

The process of this invention preferably also includes the following steps. A first grinding surface is provided on the first grinding wheel for forming a tip of desired form on the rotating wire stock and a second surface is provided on the first grinding wheel for parting a previously formed tapered multi-fluted endodontic instrument from the rotating wire stock. A second grinding wheel is provided having a plurality of depth indicating calibration groove grinding ribs extending from a periphery thereof which is rotated about a third axis. The second grinding wheel is out of grinding contact with the rotating wire stock when the first grinding wheel is in the flute grinding position.

The first grinding wheel is retracted from a flute grinding position with the rotating wire stock to a non-grinding position, and the rotating wire stock is fed forward a predetermined distance. The feed of the rotating wire stock is temporarily terminated and the first and second grinding wheels are advanced into grinding contact with the wire stock whereby the previously formed tapered multi-fluted endodontic instrument is parted from the wire stock, a tip of desired form is ground on the wire stock and depth calibration indicating grooves are ground on the wire stock. The first and second grinding wheels are next retracted whereby the first grinding wheel is returned to the flute grinding position and the second grinding wheel is returned to a position out of contact with the wire stock. Thereafter, the feed of the rotating wire stock is resumed and the instrument forming cycle is repeated.

The process preferably also includes the step of selectively accelerating the feed rate of the rotating wire stock during the grinding of flutes on the wire stock, and the wire stock is preferably fed from a coiled wire feeder which rotates on the same axis and at the same rate as the portion of the wire stock being ground.

The process also preferably includes the steps of providing a first rotated dressing wheel for dressing the peripheral surface of the first grinding wheel including the heights of the flute grinding ribs and the rolled deformed metal grinding rib thereon, and periodically or continuously maintaining the first dressing wheel in dressing contact with the first grinding wheel.

The process preferably also includes the steps of providing a second rotated dressing wheel for dressing the peripheral surface of the second grinding wheel including the heights of the depth calibration groove grinding ribs thereon, and periodically or continuously maintaining the second dressing wheel in dressing contact with the second grinding wheel.

Referring again to FIGS. 4 through 7, and particularly to FIG. 4, a second improved endodontic instrument 38 for use in performing root canal therapy is illustrated. As mentioned, the instrument 38 includes an elongate shank 90 having a proximate end 94, a pilot end 95 and a tapered peripheral surface 92 adjacent the pilot end thereof. The improved feature of the instrument 38 which makes it different from the novel instrument 2 described above and illustrated in FIG. 3 and from the prior art is that two or more portions of the peripheral surface 92 have differing tapers. That is, referring to FIG. 4, a first portion 97 of the peripheral surface 92 adjacent to the pilot end 95 of the instrument 38 has a small taper while a second portion 99 of the peripheral surface 92 has a greater taper. The differing tapers of the portions 97 and 99 can be straight uniform tapers or curved non-uniform tapers. In a preferred embodiment, the tapered peripheral surface 92 is continuously curved from its larger end near the proximate end 94 of the instrument 38 to the smaller pilot end 95 thereof. The term "uniform taper" is used herein to mean a straight surface of constant taper. The term "non-uniform taper" is used herein to mean two or more adjacent uniform or non-uniform tapers or a continuously non-uniform curved taper. The latter non-uniform taper is illustrated by the dashed line designated by the numeral 130 in FIG. 4. While the flutes 96 shown in FIG. 4 are uniform over the entire peripheral surface 92, they can be formed in separate pluralities of continuous helical flutes which contain different numbers of flutes as described above in connection with the instrument 2 illustrated in FIG. 3.

Thus, the endodontic instrument 38 includes an elongate shank having a proximate end, a pilot end and a tapered peripheral surface 92 adjacent the pilot end thereof, the peripheral surface 92 having two or more portions thereof of differing uniform taper or having a single surface of continuously diminishing non-uniform taper. A single plurality of continuous helical flutes can be formed on the portions of the peripheral surface having differing taper, or the peripheral surface having portions of differing taper can include two or more pluralities of continuous helical flutes having different numbers of flutes as described above in connection with the instrument 2 illustrated in FIG. 3.

The endodontic instruments made and used heretofore have included tapered peripheral portions containing flutes of uniform taper. The standard taper originally set by ISO and other standards was 0.02 millimeters per millimeter. In recent years, a variety of endodontic instruments having other uniform tapers have been introduced, i.e., instruments having uniform tapers of 0.04 millimeters per millimeter, 0.06 millimeters per millimeter, 0.08 millimeters per millimeter and so on. The purpose of the instruments having greater uniform tapers was to make access to the apical portion of a root canal easier. The easier access enabled the practitioner to improve and refine the preparation of the apical portion of the root canal which is considered one of the most critical parts of the endodontic procedure. Thus, present day practitioners utilize a variety of uniform tapered instruments to achieve the preparation of root canals.

Figure 7:
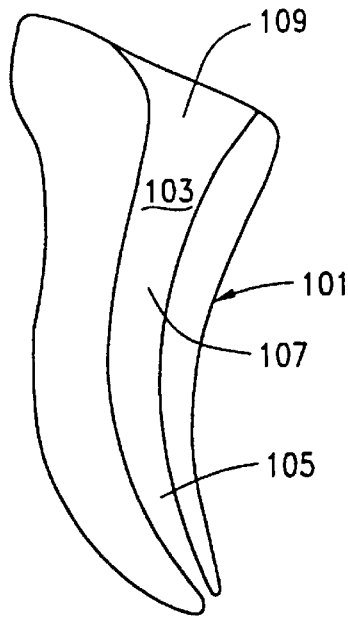
FIG. 7 is an enlarged partial side cross-sectional view of a root canal in a tooth which has been enlarged and cleaned using an endodontic instrument of this invention having fluted portions of differing taper.

Referring to FIG. 7, an enlarged cross-section of a tooth 101 having a root canal 103 which has been prepared in accordance with present day practice is illustrated. The apical portion of the root canal 105 has been widened as have the intermediate portion 107 and the coronal portion 109. To produce the root canal preparation illustrated in FIG. 7, a practitioner has heretofore used a standard 0.02 millimeters per millimeter uniformly tapered endodontic instrument for the preparation of the apical portion 105 and progressively greater tapered instruments for the intermediate portion 107 and coronal portion 109. Thus, in order for a practitioner to prepare the root canal 103, the practitioner has heretofore used large numbers of instruments with different uniform tapers.

In accordance with the present invention, the single instrument 38 can include two or more adjacent portions of different uniform or non-uniform tapers or a continuously non-uniform curved taper which increase from the pilot end to the opposite end of the tapered peripheral surface 92 thereof containing flutes 96. By using just one or a few of the improved instruments of this invention having fluted portions of differing taper, the practitioner can quickly complete a root canal preparation like that shown in FIG. 7 which heretofore would require the use of multiple instruments of uniform taper and a relatively long period of time to complete.

The multiple taper instruments of this invention are produced using the grinding process described above. The multiple portions of differing taper on the instruments are produced by varying the translation rate between the first grinding wheel and the wire stock such that the distance between the axis of the grinding wheel and the axis of the rotating wire stock increases in a manner which forms the portions of the instrument having differing taper.

As will be understood by those skilled in the art, the endodontic instruments of this invention can be formed of any suitable metal such as stainless steel or nickel-titanium alloys. Further, as previously mentioned, the number of flutes ground on the endodontic instruments can be varied over the length of the tapered peripheral surfaces on the instruments and the tapers of portions of the peripheral surfaces of individual instruments can include two or more tapers.

Thus, the present invention is well adapted to carry out the objects and attain the ends and advantages mentioned as well as those which are inherent therein. While numerous changes may be made by those skilled in the art, such changes are encompassed within the spirit of this invention as defined by the appended claims.

What is claimed is:

1. An endodontic instrument for use in performing root canal therapy on a tooth comprising:
    an elongate shank having a proximate end, a pilot end and a uniform or non-uniform tapered peripheral surface adjacent the pilot end thereof;
    a first plurality of continuous helical flutes which form cutting edges on said peripheral surface formed in and extending along a first portion of said peripheral surface; and
    a second plurality of continuous helical flutes which form cutting edges on said peripheral surface formed in and extending along a second portion of said peripheral surface adjacent to said first portion thereof, said second plurality of helical flutes containing a number of flutes different from the number of flutes in said first plurality of helical flutes.

2. The endodontic instrument of claim 1 which further comprises one or more additional pluralities of continuous helical flutes which form cutting edges on said peripheral surface formed in and extending along third and additional portions of said peripheral surface, each of said additional pluralities of helical flutes containing a number of flutes different from the number of flutes in adjacent pluralities of helical flutes.

3. The endodontic instrument of claim 1 wherein said first plurality of helical flutes contains four helical flutes and said second plurality contains three helical flutes.

4. The endodontic instrument of claim 1 which further comprises a third plurality of continuous helical flutes which form cutting edges on said peripheral surface formed in and extending along a third portion of said peripheral surface adjacent to said second portion thereof, said third plurality of helical flutes containing a number of flutes different from the number of flutes in said second plurality of helical flutes.

5. The endodontic instrument of claim 4 wherein said first and third pluralities of helical flutes contain four helical flutes and said second plurality contains three helical flutes.

6. The endodontic instrument of claim 1 wherein said first plurality of continuous helical flutes forms four spiral cutting edges on said first portion of said peripheral surface and said second plurality of continuous flutes forms three spiral cutting edges on said second portion of said peripheral surface.

7. The endodontic instrument of claim 6 wherein the cross-sectional shape of said first portion of said peripheral surface is substantially square and the cross-sectional shape of said second portion of said peripheral surface is substantially triangular.

8. The endodontic instrument of claim 1 wherein said first plurality of continuous helical flutes have smaller helix angles than the helix angles of said second plurality of continuous helical flutes.

9. In a process of producing an endodontic instrument with a predetermined taper having a plurality of flutes over a predetermined length of the instrument wherein a first grinding wheel have a plurality of flute grinding ribs extending from a periphery thereof is rotated about a first axis, a rotating wire stock is fed past the plurality of flute grinding ribs at a controlled feed rate along a second axis so that a separate spiraled flute is ground on the wire stock by each of the flute grinding ribs and the grinding wheel or the wire stock is simultaneously translated such that a distance between the first and second axes increases as the wire stock is fed whereby a single pass of the wire stock past the plurality of flute grinding ribs produces a tapered multi-fluted endodontic instruments, the improvement whereby said endodontic instrument includes successive pluralities of continuous helical flutes containing different numbers of flutes which comprises:

(a) providing an extra flute grinding rib on said first grinding wheel positioned to make grinding contact with said wire stock after each of said flute grinding ribs have made grinding contact with said wire stock;

(b) feeding said rotating wire stock past the plurality of flute grinding ribs and said extra grinding rib at a feed rate and a rotation rate such that a separate spiral flute is ground of the wire stock by each of the plurality of flute grinding ribs and said extra flute grinding rib;

(c) feeding said rotating wire stock past the plurality of flute grinding ribs and said extra flute grinding rib at a feed rate and a rotation rate such that a separate spiral flute is ground on the wire stock by each of the plurality of flute grinding ribs and said extra flute grinding rib follows the spiral path of the first flute grinding rib to make grinding contact with said wire stock; and (d) optionally repeating step (b) or both of steps (b) and (c).

10. The process of claim 9 wherein each of said plurality of flute grinding ribs and said extra flute grinding rib has a different height corresponding to a degree of taper of said endodontic instrument.

11. The process of claim 9 wherein said wire stock is fed such that said second axis is parallel to said first axis.

12. The process of claim 9 wherein said first grinding wheel has four flute grinding ribs extending therefrom including the plurality of flute grinding ribs and said extra flute grinding rib whereby a tapered endodontic instrument containing successive pluralities of continuous helical flutes having four flutes and three flutes is formed by said process.

13. The process of claim 9 which further comprises the steps of:

providing a first grinding surface on said first grinding wheel for forming a tip of desired form on said rotating wire stock and a second grinding surface on said first grinding wheel for parting a previously formed multi-fluted tapered endodontic instrument from said rotating wire stock;

providing a second grinding wheel having a plurality of depth indicating calibration groove grinding ribs extending from a periphery thereof which is rotated about a third axis;

retracting said first grinding wheel from a flute grinding position with said rotating wire stock to a non-grinding position;

feeding said rotating wire stock forward a predetermined distance;

temporarily terminating the feed of said rotating wire stock;

advancing said first and second grinding wheels into grinding contact with said wire stock whereby said previously formed tapered multi-fluted endodontic instrument is parted from said wire stock, a tip of desired form is ground on said wire stock and a plurality of depth indicating calibration grooves are ground on said wire stock;

retracting said first and second grinding wheels whereby said first grinding wheel is returned to said flute grinding position and said second grinding wheel is returned to a position out of contact with said wire stock; and resuming the feed of said rotating wire stock.

14. The process of claim 13 which further comprises the steps of:

providing a first rotated dressing wheel for dressing the peripheral surface of said first grinding wheel including the heights of said flute grinding ribs and said extra flute grinding rib thereon; and maintaining said first dressing wheel in periodic or constant dressing contact with said first grinding wheel.

15. The process of claim 14 which further comprises the steps of:

providing a second rotated dressing wheel for dressing the peripheral surface of said second grinding wheel including the heights of said depth calibration grinding ribs thereon; and maintaining said second dressing wheel in periodic or constant dressing contact with said second grinding wheel.

16. The process of claim 9 wherein said feed rate of said rotating wire stock is selectively accelerated during the grinding of said flutes on said wire stock.

17. The process of claim 9 wherein said wire stock is fed from a coiled wire feeder which rotates on the same axis and at the same rate as the portion of said wire stock being ground.

18. An endodontic instrument adapted for use in performing root canal therapy on a tooth comprising:

an elongate shank having a proximate end, a pilot end and a tapered peripheral surface adjacent the pilot end thereof, said peripheral surface having portions thereof of differing uniform or non-uniform taper;

a first plurality of continuous helical flutes which form cutting edges on said peripheral surface formed in and extending along a first portion of said peripheral surface; and a second plurality of continuous helical flutes which form cutting edges on said peripheral surface formed in and extending along a second portion of said peripheral surface adjacent to said first portion thereof, said second plurality of helical flutes containing a number of flutes different from the number of flutes in said first plurality of helical flutes.

19. The endodontic instrument of claim 18 which further comprises one or more additional pluralities of continuous helical flutes which form cutting edges on said peripheral surface formed in and extending along third and additional portions of said peripheral surface, each of said additional pluralities of helical flutes containing a number of flutes different from the number of flutes in adjacent pluralities of helical flutes.

20. The endodontic instrument of claim wherein said first plurality of helical flutes contains four helical flutes and said second plurality contains three helical flutes.

21. The endodontic instrument of claim 18 which further comprises a third plurality of continuous helical flutes which form cutting edges on said peripheral surface formed in and extending along a third portion of said peripheral surface adjacent to said second portion thereof, said third plurality of helical flutes containing a number of flutes different from the number of flutes in said second plurality of helical flutes.

22. The endodontic instrument of claim 18 wherein said first and third pluralities of helical flutes contain four helical flutes and said second plurality contains three helical flutes.

23. The endodontic instrument of claim wherein said peripheral surface is of non-uniform taper.

* * * * *